United States Patent
Murray et al.

(10) Patent No.: US 7,416,703 B2
(45) Date of Patent: *Aug. 26, 2008

(54) POLYMER BASED LANTHANIDE LUMINESCENT SENSORS FOR THE DETECTION OF ORGANOPHOSPHORUS COMPOUNDS

(75) Inventors: George M. Murray, Ellicott City, MD (US); O. Manuel Uy, Ellicott City, MD (US); Amanda L. Jenkins, Salisbury, MD (US)

(73) Assignee: The Johns Hopkins University, Baltimore, MD (US)

( * ) Notice: Subject to any disclaimer, the term of this patent is extended or adjusted under 35 U.S.C. 154(b) by 275 days.

This patent is subject to a terminal disclaimer.

(21) Appl. No.: 10/919,205

(22) Filed: Aug. 16, 2004

(65) Prior Publication Data
US 2005/0019218 A1  Jan. 27, 2005

Related U.S. Application Data

(63) Continuation of application No. 10/359,322, filed on Feb. 6, 2003, now abandoned, which is a continuation of application No. 09/300,867, filed on Apr. 28, 1999, now abandoned.

(60) Provisional application No. 60/083,365, filed on Apr. 28, 1998.

(51) Int. Cl.
G01N 7/00 (2006.01)
G01N 17/00 (2006.01)
G01N 21/00 (2006.01)
G01N 21/75 (2006.01)
G12B 13/00 (2006.01)

(52) U.S. Cl. ............... 422/91; 422/50; 422/52; 422/55; 422/68.1; 422/88; 422/82.07; 422/82.08; 422/83; 435/18; 435/19; 435/21; 436/43; 436/164; 436/166; 436/172; 436/104; 436/106; 73/1.01; 73/1.02; 73/23.2; 73/53.01

(58) Field of Classification Search ............... 422/50, 422/68.1, 91, 88, 82.07, 82.08, 52, 55, 83; 436/172, 104, 106, 43, 164, 166; 435/18, 435/19, 21; 73/1.01, 1.02, 23.2, 53.01
See application file for complete search history.

(56) References Cited

U.S. PATENT DOCUMENTS 5,026,139 A * 6/1991 Klainer et al. ............... 356/128

(Continued)

OTHER PUBLICATIONS

A.L. Jenkins and G.M. Murray. "Ultratrace Determination of Selected Lanthanides by Luminescence Enhancement." Analytical Chemistry. 1996, vol. 68, No. 17, pp. 2974-2980.*

G.M Murray, A.L. Jenkins, A. Bzhelyansky & O.M. Uy. "Molecularly Imprinted Polymers for the Selective Sequestering and Sensing of Ions." Johns Hopkins APL Technical Digest. 1997, vol. 18, No. 4, pp. 464-472.*

*Primary Examiner*—Brian J Sines
(74) *Attorney, Agent, or Firm*—Francis A. Cooch

(57) ABSTRACT

A device for measuring and detecting the organophosphonis compounds, such as a pesticides or a nerve agents is provided. The devices function by selectively binding an organophosphorous compound to a luminescent functionality-imprinted copolymer. The copolymers possess a securely bound luminescent lanthamide ion, such as $Eu^{3+}$, in a coordination complex that has been templated for the chemical functionality.

16 Claims, 11 Drawing Sheets

U.S. PATENT DOCUMENTS

| | | | |
|---|---|---|---|
| 5,581,398 A | * | 12/1996 | van Veggel et al. .......... 359/342 |
| 5,587,273 A | * | 12/1996 | Yan et al. ..................... 430/269 |
| 5,639,615 A | * | 6/1997 | Selvin et al. ................... 435/6 |
| 5,846,753 A | * | 12/1998 | Akkara et al. ................. 435/18 |
| 5,854,008 A | * | 12/1998 | Diamandis ................. 435/7.91 |
| 5,929,093 A | * | 7/1999 | Pang et al. ................... 514/332 |
| 6,316,268 B1 | * | 11/2001 | Yang et al. ................... 436/106 |
| 6,749,811 B2 | * | 6/2004 | Murray ........................ 422/91 |

* cited by examiner

POLYMER BASED LANTHANIDE LUMINESCENT SENSORS FOR THE DETECTION OF ORGANOPHOSPHORUS COMPOUNDS

CROSS-REFERENCE TO RELATED APPLICATIONS

This is a continuation of prior filed application Ser. No. 10/359,322, filed Feb. 6, 2003 now abandoned, which is a continuation of prior filed application Ser. No. 09/300,867, filed Apr. 28, 1999 now abandoned, which claims the benefit of prior filed copending provisional application Ser. No. 60/083,365, filed Apr. 28, 1998, the entire disclosures of which are incorporated herein by reference.

FIELD OF THE INVENTION

The present invention relates to sensing methods and devices employing a polymer-based lanthanide for detecting the presence of an analyte, such as, for example, an organophosphorus compound.

BACKGROUND OF THE INVENTION

A number of organophosphorus compounds are used as pesticides and nerve agents. For example, organophosphorus-based pesticides, including paraoxon, parathion and diazinon are widely used in the agriculture industry and the resultant environmental pollution is well documented. Because of their toxicity and relatively high solubility in water, organophosphorus-based pesticides pose a clear threat to drinking water and aquatic life. It is therefore necessary to monitor the levels of these materials in industrial waste waters, agricultural run-offs, and other environments to determine compliance with federal and state regulations and other safety guidelines, as well as efficiency of wastewater treatments.

In addition, organophosphorus-based nerve gases, including the chemically similar organo-fluorophosphorus compounds, sarin and soman, are of particular concern due to the increasing incidence of terrorism. Recent experiences such as the subway bombing in Japan have shown that the production of nerve agents by terrorists is a relatively simple process. Further, the use of nerve agents on troops in the Iran-Iraq war, operation Desert Stomm, coupled with concerns over the possible leakage of aging stockpiles of chemical weapons, have prompted the desire for small portable devices that can be used for real time monitoring of these substances.

The detection and quantification of these highly toxic compounds by remote sensors at very low levels in the surrounding environment are critical during their production, storage, transportation, and decontamination processes. A variety of techniques have been studied based on physical, chemical and biological approaches, but currently, there are few small and inexpensive sensors with the capability to do real time monitoring/detecting of these compounds or other atmospheric gases of military or environmental concern. Methods for the unambiguous detection and quantitation of specific gaseous species usually involve separate sampling and analysis steps using complex and expensive devices such as gas chromatography with detection by either flame ionization or mass spectrometry. Much of the technology being used, such as gas chromatography-mass spectroscopy (GC-MS) and high performance liquid chromatography (HPLC), are large (not portable), expensive or require sophisticated, often extensive analysis procedures making them undesirable for real-time field analysis.

Optical sensors for the detection of analytes generally rely on small changes in the indices of refraction in response to the presence of an analyte. Commonly used optical sensors include planar waveguides, optical fibers, metallized prisms and diffraction gratings. These and other conventional methods typically require extensive analysis procedures that can take up to 24 hours to perform. Although all these techniques have some degree of sensitivity, they lack specificity, simplicity, rapid detection and portability.

Surface acoustic wave (SAW) devices/sensors typically comprise piezoelectric crystals that detect the mass of chemical vapors absorbed into the chemically selective coating on the sensor surface. This absorption causes a change in the resonant frequency of the sensor. An internal microcomputer measures these changes and uses them to determine the presence and concentration of chemical agents. Conventional SAW sensors have coatings that exhibit unique physical properties that allow a reversible absoprtion of an analyte, such as chemical vapors. The polymer-coated sensor combined with trainable software loaded into a microcomputer to recognize chemical vapor signature patterns, completes the analysis. Although conventionally available SAW sensors meet the needs of real time analysis and offer the additional benefits of multiple gas detection capability, rugged designs, computerized control, easy operation and low cost, they typically lack selectivity, especially with respect to chemically similar organophosphorus compounds, e.g., pesticides and insecticides, thus, making false positive readings a major concern. It is therefore necessary to develop detection devices and methods that address the above and other problems.

SUMMARY OF THE INVENTION

An object of the present invention is to provide a sensor probe/transducer having a molecularly imprinted polymer containing a lanthanide-complex capable of exhibiting very narrow emission bands at wavelengths above 500 nm for detecting organophosphorus compounds.

A further object of the present invention is to provide a sensor that is capable of detecting organophosphorus compounds in parts per billion (ppb) to parts per quadrillion (ppq) levels, which is faster than other similar sensors and that is free from false positive results.

Another object of the present invention is to provide a optical based sensor device for the remote detection of an analyte.

It also an object of the present invention to provide a SAW device for detecting the presence of an analyte, to provide a selective coating based on the lanthanide based MIP to be used with a SAW device for the remote detection of an analyte.

A still further object of the present invention is to provide luminescent materials containing a lanthanide-complexes that having a relatively long-lived luminescence or phosphorescence to detect organophosphorus compounts.

As used herein, the term "organophosphorus compound" includes, but is not limited to, nerve agents (e.g., soman, sarin, tabun and VX) or pesticides (e.g., malathion, parathion, paraoxon, and diazinon).

The above and other objects are met by a spectroscopic sensor/probe comprising a lanthanide-complex bound to a molecularly imprinted polymer. By "complex" it is meant a coordination compound formed by the union of a lanthanide ion with a non-metallic ion or molecule called a ligand or complexing agent. The lanthanide-complexes of the present invention comprise at least one lanthanide ion and at least one ligand.

The molecularly imprinted polymer may be bound to a suitable substrate, such as, for example, a badge worn by a person, for the detection of analyte of interest. When the person wearing the badge enters a zone containing the analyte of interest, i.e., is exposed to the analyte of interest, the analyte binds to the lanthanide-complex in the molecularly imprinted polymer thereby causing the lanthanide-complex to luminesce when excited with blue light.

In addition, molecularly imprinted polymer of the present invention may be modified for use in the extraction and preconcentration of organophosphorus compounds prior to analysis.

In a still another embodiment, the present invention is directed to a fiberoptic sensor device for detecting the presence of at least one analyte in a sample, such as an organophosphorus compound, the sensor comprising:

at least one optical fiber means having a proximal end and a distal end for transmitting light energy, the proximal end being disposed within a probe housing, a molecularly imprinted polymer containing a lanthanide-complex disposed on or bonded to the distal end of the optical fiber means, wherein the lanthanide-complex is capable of chemically binding with said analyte, light source means for generating excitation energy, said light source means operatively associated with said optical fiber means such that said excitation light passes through said optical fiber means, and detection means operatively associated with said optical fiber means, for detecting an emission signal generated by said lanthanide complex. As used herein, the term "light" refers to optical radiation, whether ultraviolet, visible or infrared. FIG. 1 depicts a sensor device having the features of this embodiment.

In another embodiment, the present invention is directed to a surface acoustic wave sensor for detecting the presence of at least one analyte, which has been adapted to comprise a molecularly imprinted polymer having a lanthanide-complex bound thereto. In particular, the surface acoustic wave sensor of the present invention, comprises:

a film of a molecularly imprinted polymer containing a lanthanide-complex disposed on a substrate such as alumina or a piezocrystal substance such as quartz crystal;

input and output transducers disposed on the film or substrate; and a function generator operatively associated with the input transducer for generating a surface acoustic wave along a delay line. FIG. 2 depicts a sensor device having the features of this embodiment.

Additional aspects, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

A method for making a MIP transducer for use in a sensor, the method comprising:

(a) mixing a lanthanide, an organophosporus compound template and at least one imprint monomer to form a lanthanide complex;

(b) mixing the lanthanide complex with a polymerization initiator and a crosslinking agent to form a copolymer solution;

(c) partially curing the copolymer solution to obtain a partially cured copolymer;

(d) washing the partially cured copolymer to remove the organophosporus compound template to obtain the MIP transducer.

BRIEF DESCRIPTION OF THE DRAWINGS

Other objects, features and advantages of the present invention will occur to those skilled in the art from the following description of preferred embodiments and the accompanying drawings, in which.

DETAILED DESCRIPTION OF PREFERRED EMBODIMENTS

Figure 1:
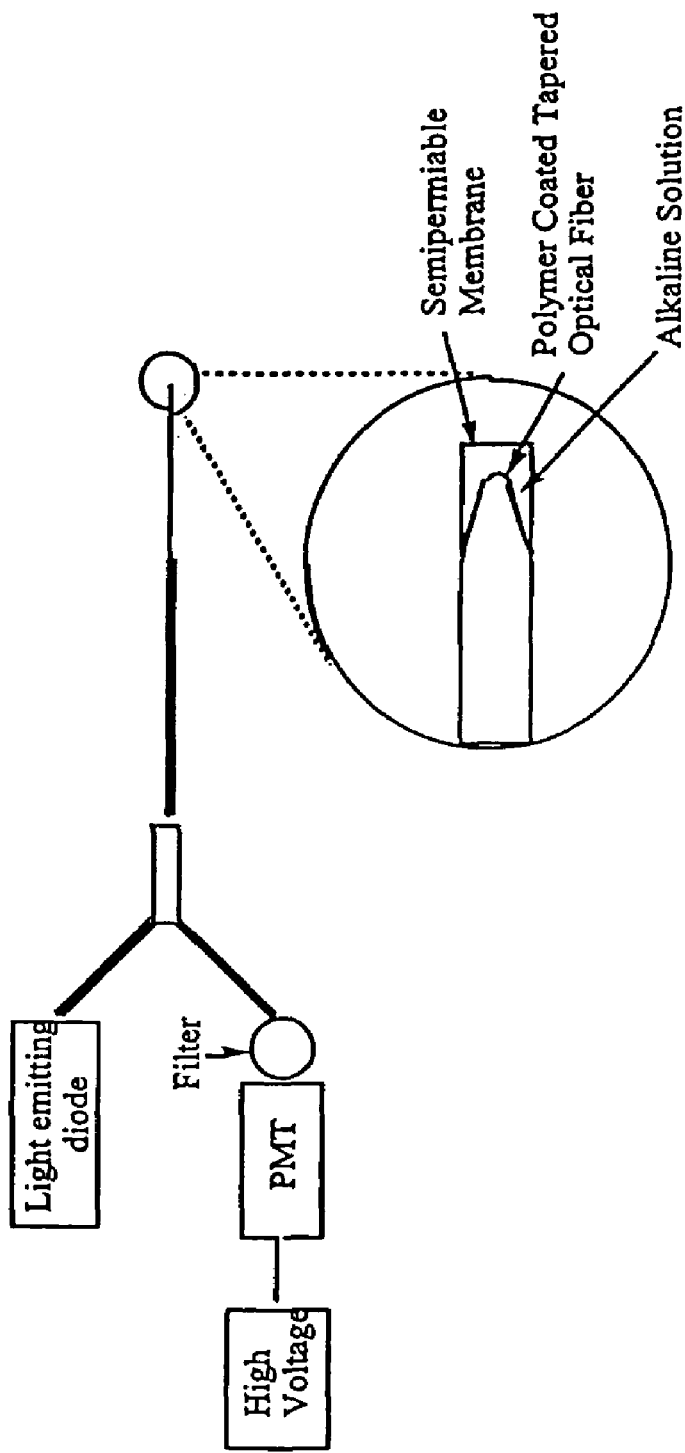
FIG. 1 is a schematic drawing of an optical sensor of the present invention.

References cited throughout this written description are incorporated herein in their entirety to more fully describe the state of the art to which they pertain.

It will be appreciated that the process steps and structures described below do not form a complete process flow for manufacturing devices encompassed within the appended claims. The present invention can be practiced in conjunction with conventionally known sensor manufacturing, and only so much of the commonly practiced manufacturing processes are included as is necessary for an understanding of the present invention.

The present invention combines the techniques of molecularly imprinting and sensitized lanthanide luminescence, thereby providing multiple criteria for selectivity for an analyte and virtually eliminating the possibility for false positive readings. The lanthanide elements, also known as the rare earth elements, consist of the elements having atomic numbers from 57 to 71. As used herein, the term "lanthanide" refers to the following elements of the periodic table: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In the present invention, a lanthanide is chosen as the transducer because the trivalent lanthanide ions have excellent spectroscopic properties such as long luminescence lifetimes and narrow bandwidths, usually only a few nanometers. Preferred lanthanide ions that exhibit a narrow-line luminescence include the +3 ions of samarium, europium, dysprosium, terbium, and neodymium, with europium and terbium being most preferred.

As used herein, the terms "molecularly imprinted molecule," "molecularly imprinted polymer" and "MIP" refer to a molecular mold-like structure that has preorganized interactive moieties complementing the spacing of binding sites on a template or template molecule. The interactive moieties can be, for example, chemical groups or affinity ligands. The geometrical organization of interactive moieties imparts selective binding characteristics for the template substance onto the imprinted polymer. The term "selective binding interactions" is intended to refer to preferential and reversible binding exhibited by an imprinted polymer for its template molecule (e.g., organophosphorus compound) compared to other non-template molecules. Selective binding includes both affinity and specificity of the imprinted polymer for its template molecule The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer, either covalently or by other interactions such as ionic, hydrophobic or hydrogen bonding, so that recognition sites for the template molecule can be provided in the substrate material. The template molecule is then removed from the substrate to leave a "cavity" or recognition site. He reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

The target or template molecule directs the positioning of the encapsulating antibody by the interactions that occur between certain sites on the target and complementary sites on the antibody. The sites that allow complementary associations are certain arrangements of atoms that exhibit an electrostatic attraction of a specific kind. These localized atomic arrangements are sometimes referred to as "functional groups." The functional groups on a molecule help to define the molecule's overall chemical properties. In general, the MIP should exhibit as closely as possible the reverse topology of the template molecule. For example, if the template molecule has an cationic group at a specific location, then the MIP should have a anionic group at that location.

The synthetic production of polymers with selective binding for a specific cation is achieved by providing polymers with cavities lined with complexing groups or "ligands" arranged to match the charge, coordination number, coordination geometry, and size of the target cation. Anion complexing polymers are made in a similar manner, but typically employ a trapped metal ion that has a large affinity for the anion in question. These cavity-containing polymers are produced by using a specific ion as a template around which monomeric complexing ligands will be self-assembled and later polymerized. The complexing ligands are ones containing functional groups known to form stable complexes with the specific ion and less stable complexes with other ions.

When lanthanide ions are chelated with appropriate ligands, a significant enhancement of the luminescence intensity is obtained. The chelated lanthanide complexes of the present invention provide a sensitive means of analysis with low limits of detection when incorporated in a MIP. For example, lanthanide ions can form complexes with various organic molecules such as beta-diketones, polyaminopolycarboxylic acids (EDTA and the like), (poly)pyridines and calixarenes. Moreover, ligands containing organic chromophores possessing suitable photophysical properties provide highly luminescent lanthanide complexes. See, Jenkins, A., et al., "Ultratrace Determination of Selected Lanthanides by Luminescence Enhancement," *Anal. Chem.*, 68(17):2974-2980 (1996) (the entire disclosure of which is incorporated herein by reference). With a careful selection of complexing ligands, metal complexes can be synthesized by mixing stoichiometric amounts of a lanthanide metal salt and the complexing ligand in an aqueous solution and evaporating to near dryness. Water or alcohol/water mixtures of the lanthanide metal and ligand in stoichiometric ratios, evaporated to dryness, are preferred to obtain near quantitative yield of the desired complex compound. To make complexes that contain target anions, it is preferred to make mixed ligand complexes that have a one-to-one stoichiometric ratio of target anion to complex. This can be accomplished by synthesizing lanthanide metal ion complexes with the proper coordination number of tightly binding ligands such that a single target analyte could bind by replacing a very weakly bound substituent.

A MIP in accordance with the principles of the present invention can be prepared using known methods. The polymerization reaction mixture for the preparation of the MIP usually consists of a template, polymerizable functional monomers, which include an effective amount of one or more crosslinking agents to provide a sufficiently rigid structure, inert solvent, and a free radical or other appropriate initiator. Mixtures of monomers and crosslinking agents can be used in the polymerization method.

In general, two approaches to the production of a molecularly imprinted polymer have been developed, and either can be used in the method disclosed herein. In the first method, a template is covalently bound to a polymerizable monomer, and after polymerization, the covalent bond is cleaved to release the template from the polymeric mold. Using this method, a selected template is attached to a polymerizable moiety using any appropriate method. The polymerizable template should contain a linkage that can be broken to release the template after the MIP is formed, without adversely affecting the MIP. The bond that is cleaved to release the template can optionally provide an additional polar or ionic site for design and imprinting of the mimic. In the second and more preferred method, polymerizable monomers arrange themselves about a template based on noncovalent interactions (such as ionic, hydrophobic, steric, electrostatic, and hydrogen bonding interactions), and after polymerization, the non-covalently bound template is simply leached or washed out.

For example, a MIP in accordance with the principles of the present invention may be formed by:

(a) mixing template molecules, i.e., an organophosphorus compound, and polymerizable imprint monomers containing a chelated lanthanide under conditions where whereby the imprint monomers bind the organophosphorus compound through interactions with the chelated lanthanide;

(b) forming the MIP from the monomers by adding a cross-linking agent to the mixture that produces covalent bonds between ligands on adjacent monomers; and (c) removing the template molecules from the MIP.

Figure 3:
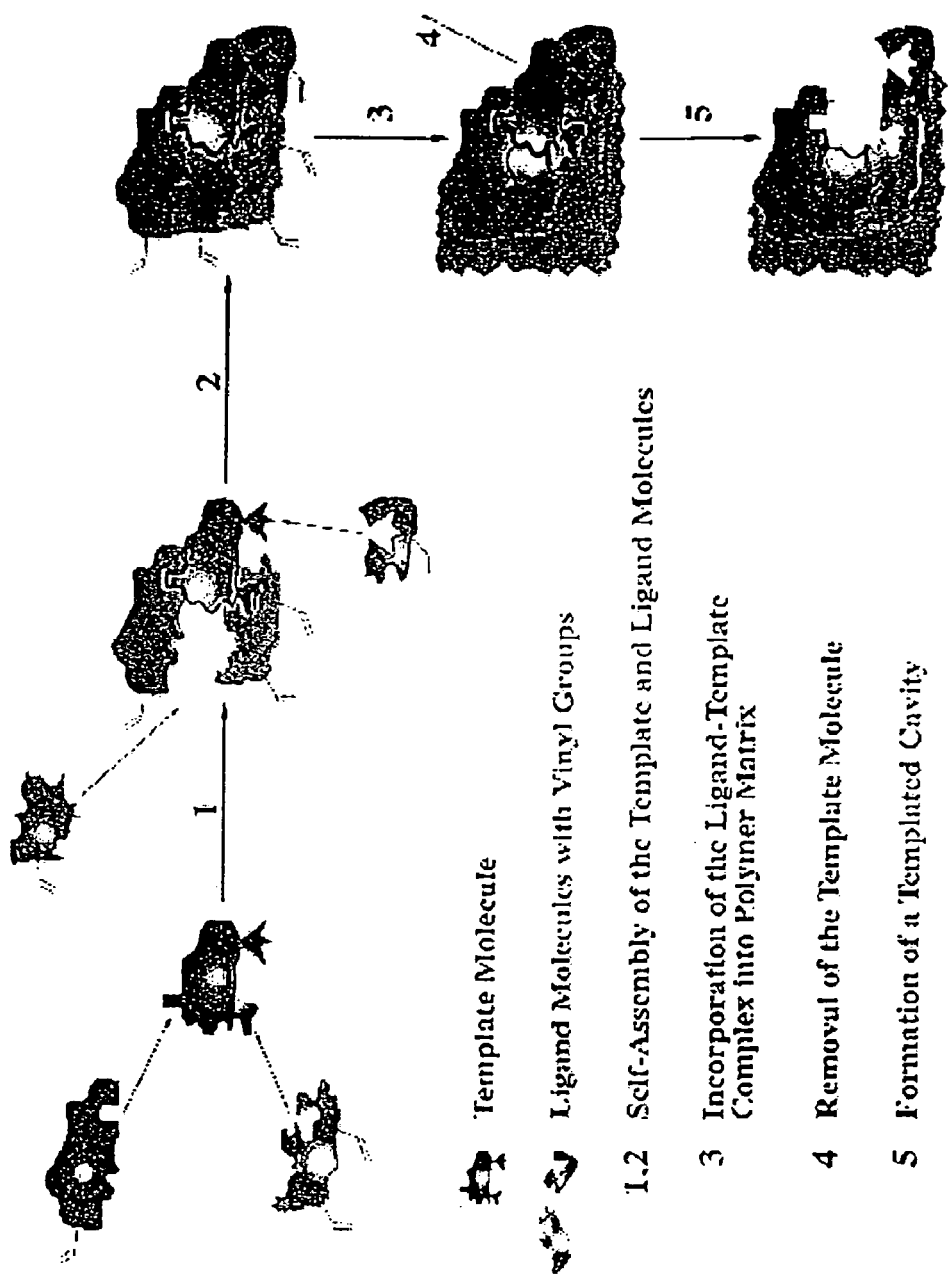
FIG. 3 is a schematic representation of molecular imprinting to obtain a molecularly imprinted polymer of the present invention.

The resultant MIP will bind the template molecule with which it was imprinted with higher affinity than other, similar, though not identical, species. FIG. 3 is a schematic representation of molecular imprinting showing self assemble of templates and ligand molecules (1,2); incorporation of the ligand-template complex into the polymer matrix (3); removal of the template molecule; and formation of the templated cavity (5). Other methods for preparing MIPs are described in U.S. Pat. Nos. 5,110,883; 5,321,102; 5,372,719; 5,310,648; 5,208,155; 5,015,576; 4,935,365; 4,960,762; 4,532,232; 4,415,655; and 4,406,792, the entire disclosures of which are incorporated herein by reference.

It will be appreciated that a key step in making a molecularly imprinted polymer is to form a complex that will survive the polymerization process and leave behind a suitable set of binding sites when the templating species is removed. To form such a complex, ligands must be chosen that exhibit sufficiently large affinities to resist dissociation. The success of the end product hinges on the selection of the ligating monomer. In addition, the polymerization process must provide sufficient rigidity to effect structural "memory" but be sufficiently flexible to allow removal of the template ion.

Figure 4:
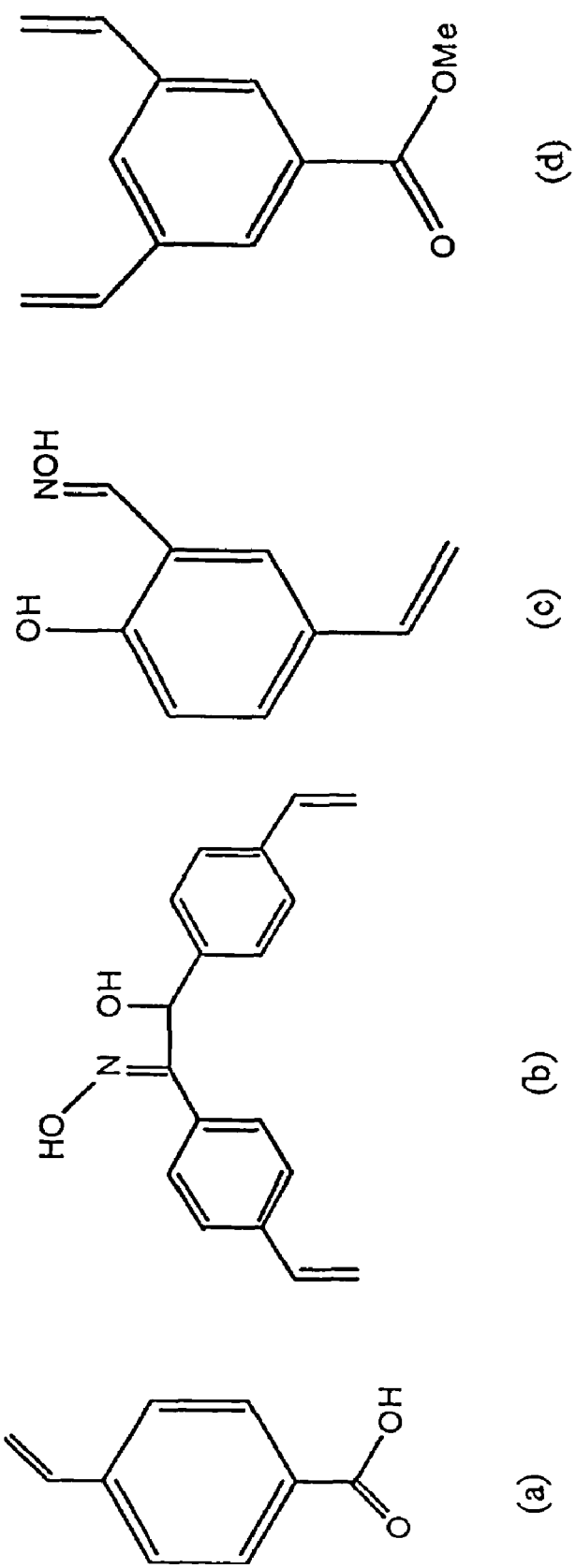
FIG. 4 depicts structural representations of ligand monomers that may used in accordance with the principles of the present invention.

Any suitable monomer that provides an accurate imprint of the template molecule on polymerization may be used for the synthesizing a MIP in accordance with the principles of the present invention. For example, structural representations of preferred monomers are depicted in FIG. 4, namely (a) 4-vinyl benzoic acid, (b) 2-hydroxy-1,2-di-4-vinylphenyletha-none (benzoin oxime vinyl derivative), (c) 4-vinyl-2-hydroxybenzaldchyde oxime (vinylsalicylaldoxime) and (d) melhyl-3,5-divinyl benzoate (MDVB). Examples of other suitable monomers for use in either of the two approaches discussed above, include, but are not limited to, those described in the references cited in this written description and the Examples provide below. Further suitable non-limiting examples of monomers that can be used for preparing a MIP of the present invention include: methylmethacrylate, other alkyl methacrylates, alkylacrylates, ally or aryl acrylates and methacrylates, cyanoacrylate, styrene, .alpha.-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-.alpha.-acryloxy-.beta., .beta.'-dimethyl-g-butyrolactone; N-acryloxy succinimiide N-acryloxytri.s(hydroxymethyl) aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl) ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4-dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; .beta.-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrenc; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl4-pentenal; 2,4-dimethylstyrene; 2,5-dimethylstryene; 3,4-dimethylstryene; divinyl benzene; 1,3-divinyltetramethyl disiloxane; 8,13-divinyl-3,7, 12, 17-tetramethyl-21H,23H-porphine; 8,13-divinyl-3,7, 12,17-tetramethyl-21H,23H-propionic acid; 8,13-divinyl-3,7, 12,17-tetramethyl-21H,23H-propionic acid disodium salt; 3,9-divinyl-2,4,8,10-tetraoraspiro[5,5]undecane; divinyl tin dichloride; 1-dodecene; 3,4-eoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl) tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7, 11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy)ethyl trimethyl ammonium methylsulfate; 2-methoxy propene (isopropenyl mcthyl cther); methyl-2-(bromomethyl)acrylate; 5-methyl-5-hexen-2-one; methyl methacrylate; N,N'-methylene bisacrylamide; 2-methylene glutaronitrile; 2-methylcne-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-17 pentene;

.alpha.-methyl styrene; t-a-methylstyrene; t-.beta.-methylstyrene; 3-methylstyrene; methyl vinyl ether; methyl vinyl ketone; methyl-2-vinyloxirane; 4-methylstyrene; methyl vinyl sulfonee; 4-methyl-5-vinylthiazole; myrcene; t-.beta.-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2, 4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3-chloroacrylic acid; 2-trifluoromethyl propene; 2-(trifluoromethyl)propenoic acid; 2,4,4'-trimethyl-1-pentene; 3,5-bis (trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl triacetoxysilanc; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl-vinyl phosphonium bromide); vinyl tris-(2-methoxyethoxy)silane; vinyl 2-valerate and the like.

Acrylate-terminated or otherwise unsaturated urethanes, carbonates, and epoxies can also be used in the MIP. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Crosslinking agents that lend rigidity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, tricthylene glycol diacrylate, triethylene glycol dimethacrylate, hexanediol dimethacrylatc, hexanediol diacrylate, and the like.

Any ratio of simple monomers to crosslinking monomers can be used that provides a structure of appropriate integrity. Those skilled in the art can select suitable ratios of monomers to provide the desired structural integrity.

Figure 5:
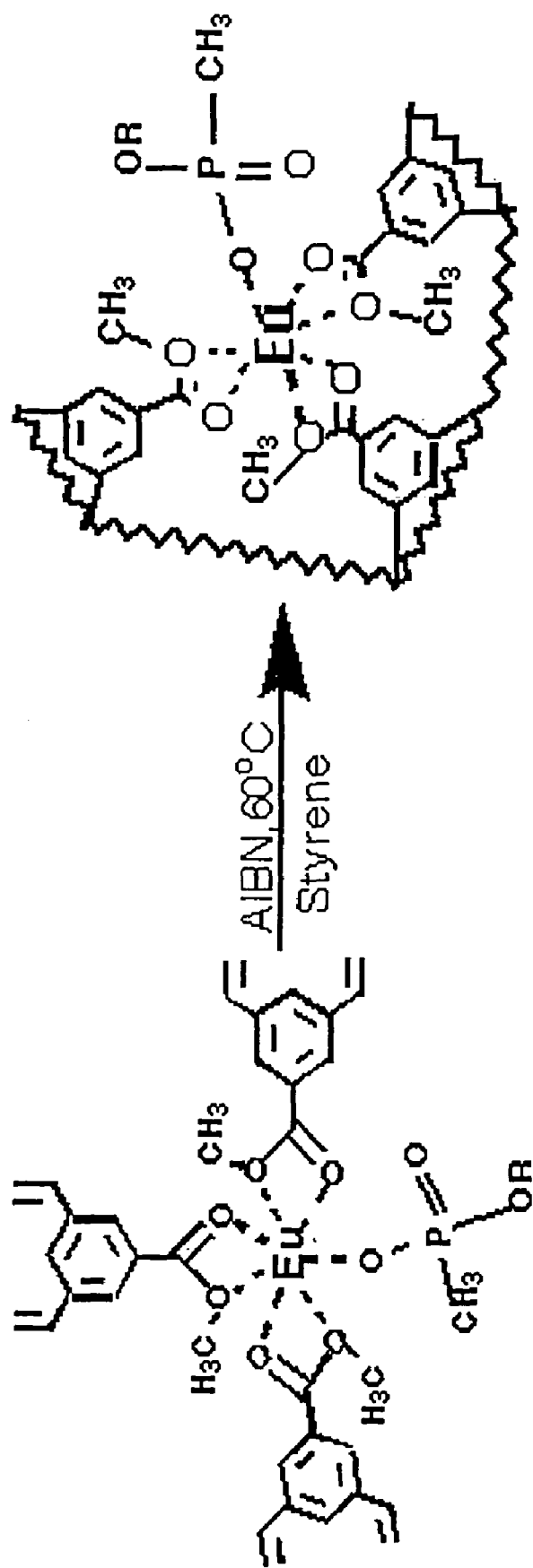
FIG. 5 shows a polymerization reaction scheme for the production of a molecularly imprinted polymer in accordance with the principles of the present invention.

While free radical polymerization is preferred, monomers can also be selected that are polymerized cationically or anionically. Polymerization conditions should be selected that do not adversely affect the template molecule. Any UV or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile (AIBN), t-butyl peracetate, cumyl peroxide, t-butyl peroxide, t-butyl hydroperoxide, bis(isopropyl)peroxydicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenyl-acetophenone, and phenothiazine and diisopropylxanthogen disulfide. See, e.g., FIG. 5.

When polymerization is complete, the crosslinked polymer may be washed, cryogenically ground to a uniformly fine powder, and extensively eluted with nonpolar solvents to remove unreacted complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction. Polymers used in the construction of optical sensors may be prepared in situ on the distal end of an optical fiber whose surface is prepared by binding a polymerizable agent on the surface.

Figure 6:
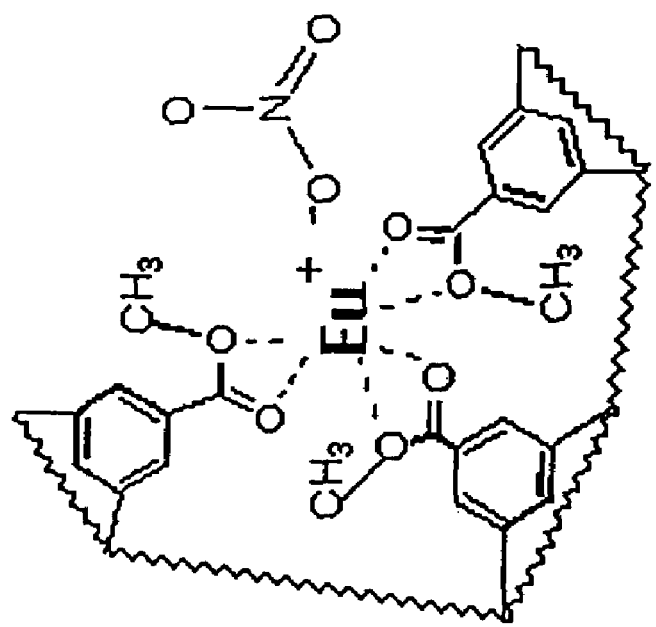
FIG. 6 shows a reaction scheme for the removal of a template molecule from a molecularly imprinted monomer to obtain a templated cavity.
Figure 6:
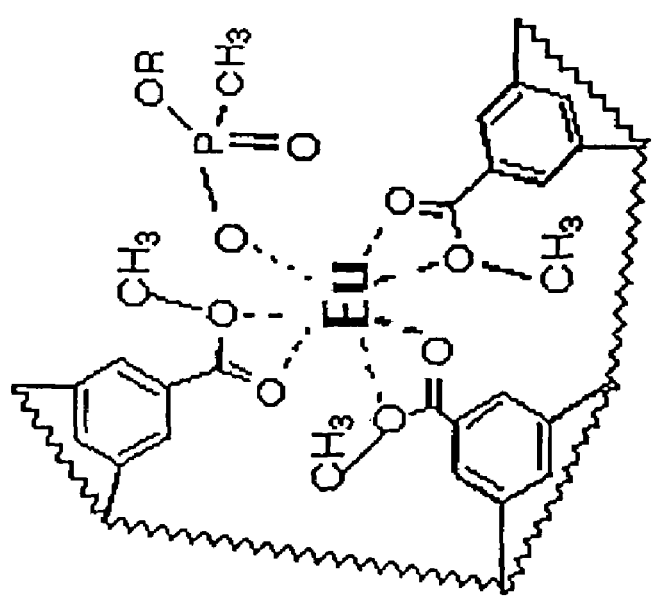

After polymerization, the template molecule may be removed in a manner that does not adversely affect the imprinted cavity. If the template is covalently bound, it is removed using the mildest conditions possible for the cleavage of the covalent bond. To accomplish this, acetone or other suitable organic solvent may be used to swell the resultant polymers, allowing greater access to the coordinated metal ions because templated resins have a relatively low amount of functionalization and are primarily nonionic matrices. For organophosphorus compound templated resins, subsequent to the removal of unwreacted monomer, a 1 N aqueous acidic solution may be mixed into the acetone washes, with increasing aqueous acidic phase in each sequential wash, to remove the template molecule from the cavities. Preferably an acidic solvent is used having a pH of about 4.5 or less. See, e.g. FIG. 6.

A method for making a MIP transducer for use in a sensor, the method comprising:

(a) mixing a lanthanide, an organophosphorus compound template and at least one imprint monomer to form a lanthanide complex;

(b) mixing the lanthanide complex with a polymerization initiator and a crosslinking agent to form a copolymer solution;
(c) partially curing the copolymer solution to obtain a partially cured copolymer;
(d) washing the partially cured copolymer to remove the organophosporus compound template to obtain the MIP transducer.

As can be appreciated by the skilled artisan, the preferred synthetic schemes and embodiments described above and in the Examples below are not intended to comprise a comprehensive list of all means by which the MIPs described and claimed herein may be synthesized. It will be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described throughout this written description may be performed in an alternate sequence or order to obtain the present invention.

In a preferred embodiment, MIP may be bound to a suitable substrate, such as, for example, a dosimeter-like badge worn by a person, for the detection of an analyte of interest. When the person wearing the badge enters an area containing the analyte of interest, i.e., is exposed to the analyte of interest, the analyte binds to the lanthanide-complex in the molecularly imprinted polymer thereby causing the lanthanide-complex to luminesce when excited with a laser or LED.

In a another preferred embodiment, the present invention is directed to a fiber optic sensor device for detecting the presence of at least one analyte in a sample, such as an organophosphorus compound, the sensor comprising:
  at least one optical fiber means having a proximal end and a distal end for transmitting light energy, the proximal end being disposed within a probe housing,
  a molecularly imprinted polymer containing a lanthanide-complex disposed on, or bonded to, the distal end of the optical fiber means, wherein the lanthanide-complex is capable of chemically binding with said analyte,
  light source means for generating excitation energy, said light source means operatively associated with said optical fiber means such that said excitation light passes through said optical fiber means, and
  detection means operatively associated with said optical fiber means, for detecting an emission signal generated by said lanthanide complex.

As used herein, the term "light" refers to optical radiation, whether ultraviolet, visible or infrared. Suitable non-limiting examples of light source means include an argon laser, blue laser, tunable laser, light emitting diode (LED) and the like.

Suitable non-limiting examples of detection means include a spectrophotometer, spectrometer (gas or mass), photomultiplier tube, monochromator equipped with a CCD camera, filters, the naked eye and the like.

In this embodiment, the portable device may employ a modulated light emitting diode (LED) for excitation and a small photosensor module for detection, with the output going to a microprocessor controlled grated integrator. In addition, an optical multiplex switch may be incorporated into the design so that many sensors can be coupled to one control system, which will allow monitoring of a large area such as found in a building, subway station, shopping mall, airport, etc.

In use, an organophosphurus compound, if present, binds to the lanthanide-complex in the molecularly imprinted polymer causing it to luminesce under appropriate excitation. Light from the light source means travels along the optical fiber to its distal end where it undergoes a change caused by interaction with the lanthanide-complex. The modified light returns along the same or another fiber to the detection means which interprets the returned light signal. Detection is based on the change that occurs in the lanthanide's luminescence spectrum when an analyte binds to the lanthanide-complex.

Optionally, the distal end (working end) of the sensor may be enclosed within a semi-permeable membrane to separate the analyte-containing media being analyzed from the probe. One function of the membrane is to separate, as far as possible, the analyte (i.e., those components in a sample that can bind to the probe) from interferents (i.e., compounds which may be present but are undesirable because they either interfere with the progress of the desired determination reactions or take part in reactions of their own which compete with those of the component sought and distort or overwhelm the signals that are to be measured). If the sensor probe is configured to detect the hydrolysis products of the nerve agents soman and sarin, then the semi-permeable membrane may be impregnated with an alkaline solution or coated with a nonvolatile alkaline oil, to catalyze the hydrolysis of the nerve agents soman and sarin to their respective hydrolysis products.

In yet another preferred embodiment, the present invention is coated on a SAW sensor for detecting the presence of at least one analyte. The SAW sensor comprises a molecularly imprinted polymer having a lanthanide-complex bound thereto. In particular, the surface acoustic wave sensor of the present invention, comprises:
  a film of a molecularly imprinted polymer containing a lanthanide-complex disposed on a substrate such as alumina or a piezocrystal substance such as quartz crystal;
  input and output transducers disposed on the film or substrate; and
  a function generator operatively associated with the input transducer for generating a surface acoustic wave along a delay line.

Figure 2:
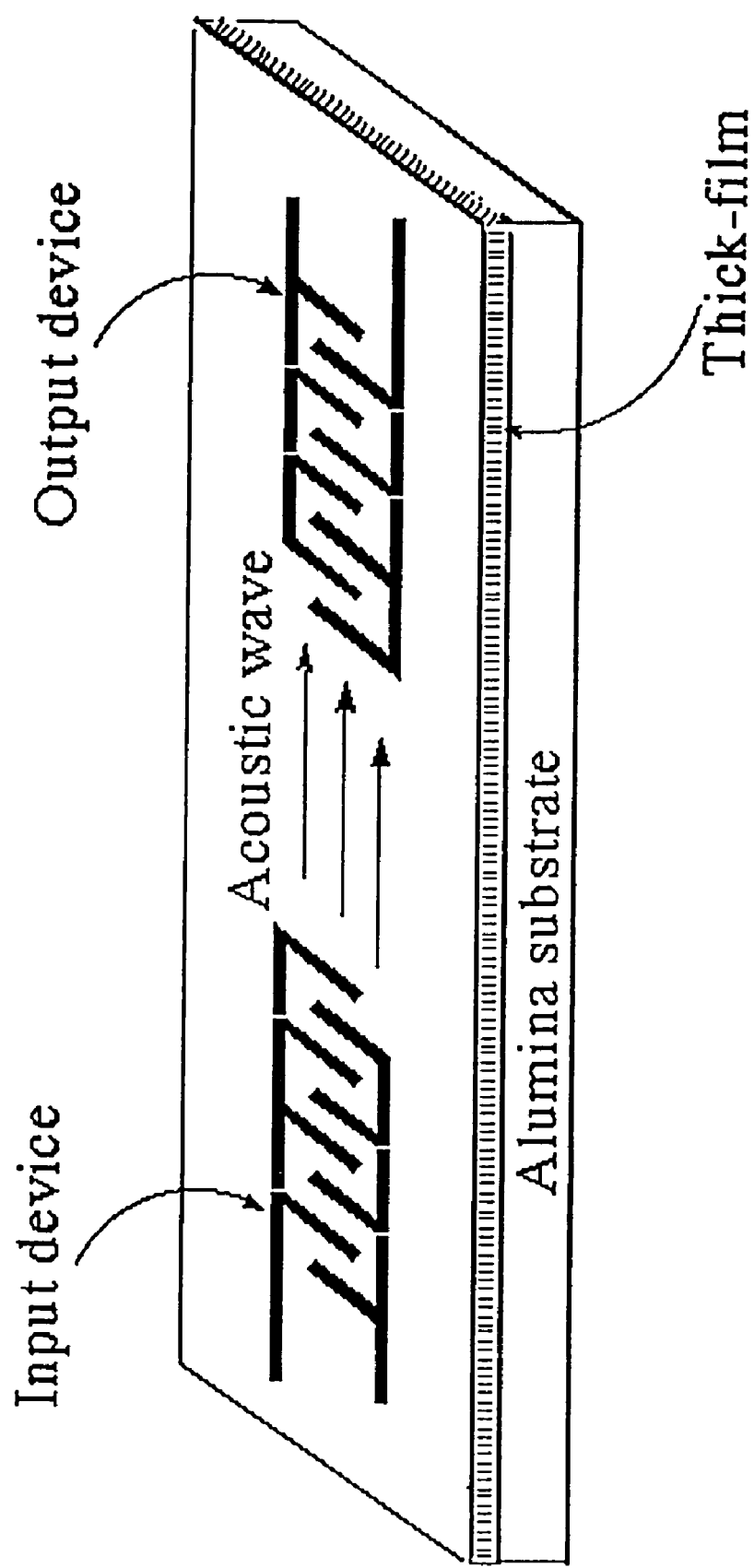
FIG. 2 is a schematic drawing of a SAW sensor of the present invention.

FIG. 2 depicts a SAW device in accordance with the present invention. In use, the function generator supplies a pulse modulated sine signal to the input transducer. The generated surface acoustic wave is modulated in the same way as the input electrical signal. The acoustic energy is converted again into an electric signal in the output transducer which may be connected to a microcomputer. This signal brings information about the amplitude, phase, frequency and velocity of propagation of the surface acoustic wave on the film. When an analyte binds to the lanthanide-complex, the sensor substrate will perturb the surface acoustic wave propagation along a so called delay line, which is then detected using conventional means, such as an PMT, microcomputer, etc.

EXAMPLES

The present invention will be further illustrated in the following, non-limiting Examples. The Examples, which exemplify a fiber optic sensor for detecting the hydrolysis products of the nerve gases soman and sarin, are illustrative only and do not limit the claimed invention regarding the materials, conditions, process parameters and the like recited herein.

It should be noted that open air testing of actual chemical agents has been forbidden since the late 1960's when an agent was inadvertently sprayed on desert grazing land in Utah. Therefore, an exemplary device designed for the detection of agents either can not easily be tested, or it must be designed to respond to a surrogate material, increasing the possibilities for false alarms. In order to circumvent this problem, the sensor described below was designed to measure the hydrolysis product of soman, pinacolylmethylphosphonate (PMP). This approach allows for the indirect detection of the agents since the agents will rapidly hydrolyze in water. The inclusion of a hydrolyzing surface coating can be used if gas phase sensing is required. This scheme minimizes the hazards and difficulties associated with directly working with these toxic agents. The polymers used in the sensor were templated for PMP because since the polymer bound functional end of the molecule is the same for the hydrolysis product of either soman or sarin.

Unless otherwise indicated, the reagent materials were obtained from commercial suppliers and used without further purification. Analytical reagent grade chemicals were used along with deionized water to prepare solutions. PMP and sodium phosphate were obtained from Aldrich (Aldrich, Milwaukee, Wis. 53233). Neat liquid standards of Phosdrin and Dichlorvbs as well as solid standards of Methyl Parathion and Dimethoate were obtained from Supelco (Supelco Chromatography Products, Bellefonte, Pa. 16823). Malathion, Thionazin, and Dibutyl Chlorendate were obtained as neat liquid standards from Radian (Radian International, Austin, Tex. 78720).

Instrumentation. Luminescence was excited using a model 60×argon ion laser (MWK Industries, Corona, Calif.). Spectra were collected using an f/4, 0.5 m monochromator (Chromex, Albuquerque, N.Mex.) equipped with a Model ST-6 CCD (Santa Barbara Instruments Group, Santa Barbara, Calif.) using Kestrel Spec Software (K&M Co., Torrance, Calif., USA). Spectra were also obtained with an Ocean Optics S2000 Miniature Fiber Optic Spectrometer (Ocean Optics, Dunedin, Fla. 34698) equipped with a 1200 line holographic grating, permanently installed 100 micron slits and a 440 nm cutoff filter. Molecular absorbance spectra were obtained using a UVVIS spectrophotometer (Beckman Instruments Inc., Fullerton, Calif., USA). Radiative lifetimes and quantum efficiencies were measured using a Quanta Master Spectrophosphorimeter (Photon Technologies Inc., Ontario, Canada). Electron micrographs were obtained using a Topcon DS-701 dual stage scanning electron microscope (SEM) (Topcon, Paramus, N.J. 07652). Metal concentrations were determined using a Hewlett Packard 4500 Series ICP-MS model G1820A (Hewlett Packard, Wilmington, Del. 19808). Graphs and spectra were plotted and calculations performed using Igor Pro Software (WavcMetrics Inc., Lake Oswego, Oreg. 97035).

Example 1

Compound Preparation

Lanthanide complex compounds were synthesized using a stoichiometric ratio of one mole of europium to one mole of PMP and 3 to 7 moles of ligating molecules. (The number of ligating species depended on the number of ligands needed to acquire 9 coordinate $Eu^{3+}$.) The calculated amount of each ligand was added to the europium solutions. PMP was added to a 50/50 water-methanol mixture to enhance its solubility, then added to the europium/ligand mixture. The resulting solutions were stirred approximately 2 hours, then left to evaporate the solvent. Analogous compounds without PMP were also synthesized. $Eu(DVMB)_3PMP(NO_3)_2$ and $Eu(DVMB)_3(NO_3)_3$ were synthesized in the manner detailed above. (Divinyl methyl benzoate (DVMB) was freshly prepared.:before use since it readily polymerizes.) Shea, K. J., et al., *Macromolecules*, 24:1207-1209(1991). The stoichiometry of $Eu(DVMB)_3PMP(N_3)_2$ was verified using ICP-MS Eu 16.12% (calculated 16.36%). Low temperature crystal spectra of both compounds were collected from 575 to 700 nm using 465.8 nm excitation. Spectra were interpreted to determine the symmetry changes associated with PMP inclusion. Lifetimes and time resolved luminescence spectra of $Eu(DVMB)_3PMP(NO_3)_2$ and $Eu(DVMB)_3(NO_3)_3$ were obtained and quantum efficiencies were evaluated with respect to a reference perchlorate solution. Stein, G., et al., *Chem. Phys.*, 62(1):208-213 (1975).

Example 2

Polymer Preparation

Styrenic block copolymers were prepared and the optimal mole percent complex for the preparation of the polymer coating determined. Polymers were prepared by dissolving 1 to 5 mole percent complex compound in 94-98 mole percent styrene. Approximately 1 mole percent of azobisisobutylnitrile (AIBN) was added as an initiator to the mixture described in Example 1. Crosslinked polymers were also prepared using 3 mole percent compound with 1-5 mole percent of a crosslinking agent divinyl benzene (DVB), styrene and AIBN. The resulting solutions were placed in glass vials, purged with nitrogen, and sealed using parafilm and screw on tops. The resulting translucent polymers displayed a slight yellow tint and upon excitation with a uv lamp, displaying the characteristic red-orange luminescence of curopium. The best results were obtained from the 3 mole percent complex. The 610 nm peak was intense and easily discernible from other Eu(III) peaks. Lower percent complex polymers displayed weak luminescence characteristics and higher percent polymers although more intense overall, had a diminished analyte peak. Polymers with greater than 5 mole percent complex were not used since they tend to become opaque, reducing optical transduction.

The polymers were sonicated for 2-4 hours at 60° C. (Sonication is believed to help maintain homogeneity in the polymer.) Zeng, X.; Murray, G. M. *Separation Science and Technology*, 31:2403-2418 (1996). After sonication, the partially polymerized material was placed in an oven at 60° C. and allowed to cure overnight. The resulting block copolymers were ground to expose a larger surface area of the polymer and facilitate the removal of the imprinting ion. Once ground, the template ion is removed in two steps (Id.): (1) swelling in water and gradually increasing amounts of methanol (Helferich, F., *Ion Exchange*; McGraw-Hill: New York, 511(1962)) to remove unreacted monomer and expand the polymer pores, (this produces accessible sites and facilitates the removal of the imprinting ion, and (2) removal of the imprinting ion by acid washing. Acid washing (pH of about 4.5) facilitates the removal of PMP and leaves in its place a weakly coordinated nitrate.

The optimal conditions for swelling the polymer include a series methanol/water washes, followed by washing with a weak nitric acid solution. The spectrum of the washed polymer shows the 610 nm peak was no longer visible, demonstrating that PMP was effectively removed. A small residual peak at 610 nm was viewed in some of the polymers resulting from some hydrolysis product trapped in the deeper levels of the polymer. The overall intensity of the polymer's luminescence also decreases upon washing since the nitrate is only weakly coordinated, possibly allowing water to enter the coordination sphere of the lanthanide. The washed polymer was tested for its ability to rebind PMP by exposing it to a 150 ppm PMP solution in aqueous 1M NaOH and obtaining its luminescence spectra. The 610 nm peak was observed in the spectra.

Example 3

Fiber Optic Sensor

A fiber optic sensor comprising a 400 micron optical fiber (Thor Labs, Newton, N.J., 07860) with the polymeric sensing element chemically bound on its distal end was constructed. The fibers were prepared by terminating one end with an SMA connector and removing the cladding from and polishing the distal end using the procedures outlined in the "Thor Labs Guide to Connectorization and Polishing of Optical Fibers". The tips were dipped into the chemically initiated viscous copolymer described in Example 2 leaving a uniform layer on the fiber. The polymer finished curing under a small UV lamp, overnight. Coated fibers were conditioned in a manner similar to the ground polymers as outlined above. Final versions of the sensor were prepared using a tapered fiber created by heating it in an air/acetylene flame and manually pulling the stripped end. The tapered fibers were much more efficient at coupling the evanescent field to the polymer and gave greatly improved results.

Figure 7:
FIG. 7 is a scanning electron micrograph of a MIP coated vinylized optical fiber.

Differing thicknesses of the polymeric coating were used to evaluate the effects of polymer thickness on response time, background signal and signal intensity. Thickness was controlled by the number of times the fiber was dipped into the viscous polymer. Digital images of the coated and uncoated fibers were taken using a scanning electron microscope (SEM). The fibers were analyzed at low acceleration voltages with no prior sample preparation. (Low acceleration voltage was used to minimize charging artifacts on the fibers.) The images were acquired using SM701_AP software available from the vendor. During the imaging, measurements of the polymer thickness were performed (FIG. 7), and the average thickness resulting from each dip was estimated to be between 15 and 20 μm. It was observed that increasing the thickness of the coating undesirably increased the time required for response and the intensity of a residual 610 nm peak in the background. This is consistent with the fact that thicker coatings have cavities that are deeper in the polymer and are relatively inaccessible. Thus, a larger amount of PMP could remain trapped in the polymer increasing the residual peak. A thickness of four coats, approximately 60 to 80 μm was determined to be optimal for the design of the sensors since it gives an 80% response within a reasonable time (less than 8 minutes).

Example 4

Analysis

Measurements for the calibration data, pH study, and interference testing of the sensor described in Example 3 were all performed using the same fiber. The analytical figures of merit were obtained using serial dilutions of a 100 ppm PMP standard in 0.01 M NaOH.

Luminescence was excited using the argon laser and the active end of the sensor was placed in a quartz cuvette containing one of the sample dilutions. Two argon ion excitation wavelengths 465.8 and 488 nm, were used with the polymer. The spectrum of the sensor excited with the 465.8 nm laser line displayed better spectral resolution of the 610 nm analyte peak from the 615 nm luminescence peak of the parent europium. The luminescence of the compound excited at 465.8 nm was also more intense. This increase indicates that excitation using the 465.8 nm line results in a near resonant excitation transition from the ground $^7F_0$ level to the $^5D_2$ level. As a result, 465.8 nm was chosen as the excitation wavelength for the sensor. Spectra were collected at each concentration after the sensor had equilibrated for 10 minutes. The sensor was rinsed with deionized water between each concentration. Standards were analyzed in order of both increasing and decreasing concentration in order to demonstrate the reversibility of the sensor. Calibration curves were obtained and linear regressions were performed.

The response of the sensor and the pH dependence of the temporal response were evaluated. A series of 100 ppm pinacolylmethylphosphonate standards with pH values ranging from 4.5 to 13.0 were prepared from the stock standard through the addition of 1.0 M nitric acid or 1.0 M sodium hydroxide. The sensor was placed in a cuvette with each solution and spectra collected at a variety of exposure times. Response was evaluated through a comparison of peak intensity at each time with pH.

A series of pesticide and insecticide standards along with a phosphate buffer solution were tested as possible interference. Standard 1000 ppm solutions were prepared by the dissolution and/or dilution of the samples in deionized water when possible. The pesticides with limited solubility in water were prepared using a 50:50 water/methanol mixture. The pH of each of the solutions was adjusted to 12 using 1 M sodium hydroxide. Spectra from the fiber for each analyte were taken at regular intervals for 60 minutes. The resulting spectra were then compared with the response from the sensor in 100 ppm PMP. The sensor was cleaned using 1 M nitric acid and rinsed with deionized water between each analysis.

Figure 8:
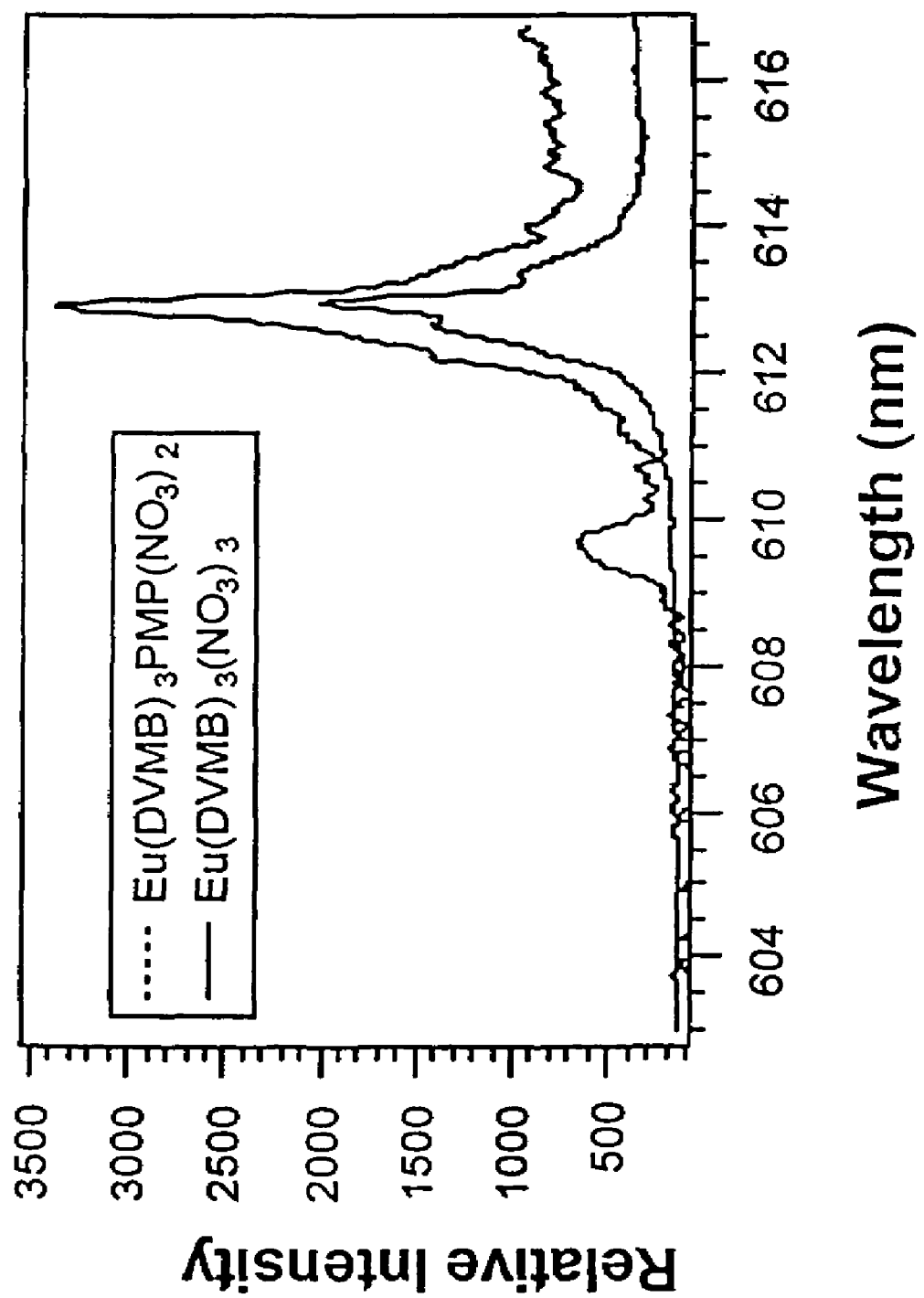
FIG. 8 is laser excited luminescence spectra of $Eu(DMMB)_3(NO_3)_3$ and $Eu(DMMB)_3(NO_3)_3(PMP)$ crystalline solids excited at 465.8 nm.

$Eu(DMMB)_3PMP(NO_3)_2$ demonstrated a relatively easily discernible spectral difference. See FIG. 8. The luminescence intensity of this compound was not as large as some of the other candidates, however, the clarity of the spectral difference between the compound with and without the hydrolysis product made detection based on the spectrum a relatively simple process. In order to verify that the new peak was not simply a result of a mixture of $Eu(MP)_3$ and the complex, $Eu(PMP)_3$ was prepared and its luminescence spectrum generated. The peak at 610 nm in the $^7F_2 \leftarrow ^5D_0$ manifold of $Eu^{3+}$ for the compound was clearly not in the spectrum of $Eu(PMP)_3$. The $Eu(PMP)_3$ displayed weak luminescence and poor resolution. The $Eu(PMP)_3$ spectra strongly suggests that the peak at 610 nm was due to the addition of the hydrolysis product to the compound and not an impurity.

Low temperature (77K) luminescence spectra were analyzed using 465.8 nm excitation to determine the site symmetry of the europium in the compounds. Changes in the spectra were used to elucidate the effects of the substitution of PMP for nitrate. Structural inferences were based on the splitting patterns observed in the $^7F_n \leftarrow ^5D_0$ (where n=0 to 5) manifolds of the europium spectrum. Stump, N. A., et al., *Spectroscopy Letters* 28:1421 (1992).

Lifetime determinations were performed on the DMMB compounds. Using weighted regression, the lifetimes for $Eu(DMMB)_3PMP(NO_3)_2$ and $Eu(DMMB)_3(NO_3)_3$ were calculated to be 337.6 μsec and 312.5 μsec, respectively. Quantum efficiencies for the compounds were determined using a europium perchlorate compound of known quantum efficiency, 1.9%. The determination was based on the ratios of the peak areas in the 500-800 nm region of the spectra of three compounds. The quantum efficiencies with and without PMP were 8.54% and 7.76%, respectively. The molar absorptivities were the same for all the compounds (0.0083 L cm$^{-1}$ moles$^{-1}$). The spectrum of the analogous divinyl compounds were examined and found to produce the same spectra as the dimethyl complex. The position of the 610 nm band of interest remained unaffected by the vinyl substitution.

The performance of the fiber optic sensor with the ¼ meter monochromator was evaluated. The sensor used to determine the limit of detection consisted of a 400 μm optical fiber with a tapered end. A 50-75 μm layer of the 3 mole percent polymer was directly deposited on to the end. The fiber was cleaned using the method previously described. Using 1 mW of 465.8 mm for excitation, 200 μm slits with the monochromator, and an exposure time of 5 seconds, the luminescence spectrum of the sensor in a series of PMP solutions at pH 13, was obtained. The response of the sensor to increasing concentrations of PMP exhibits an increase in the luminescence intensity of the primary europium band as well as an increase in the intensity of the analyte peak. This increase in the luminescence is indicative of the rebinding of the PMP product into the primary coordination sphere of the lanthanide and the exclusion of water. The structural determination performed for the characterization of the compound also supports this conclusion. The resulting peak areas in the 609 to 611 nm spectral region of the analyte were calculated using Igor Pro Software, and plotted as a function of concentration. Peak areas have been shown to provide a longer, more linear calibration curve than direct peak height, since the band widths as well as the peak heights of the lanthanides increase as a function of concentration. Linear regression analysis was performed on the data and a limit of detection of 750 ppq calculated. The analytical figures of merit for the sensor with the benchtop apparatus are given in Table 1. Concentrations below 750 ppq show no change in the intensity of either band. The residual 610 nm band remains visible even when the sensor is cleaned, and should be subtracted out with the background for application purposes. Variations in the residual peak, the background, or other slight differences between sensors appear to have little effect on the overall calibration curve, linear dynamic range and limit of detection. The typical 80% response time for the sensor was less than 8 minutes.

Example 5

Response Time and pH Dependence

Figure 9:
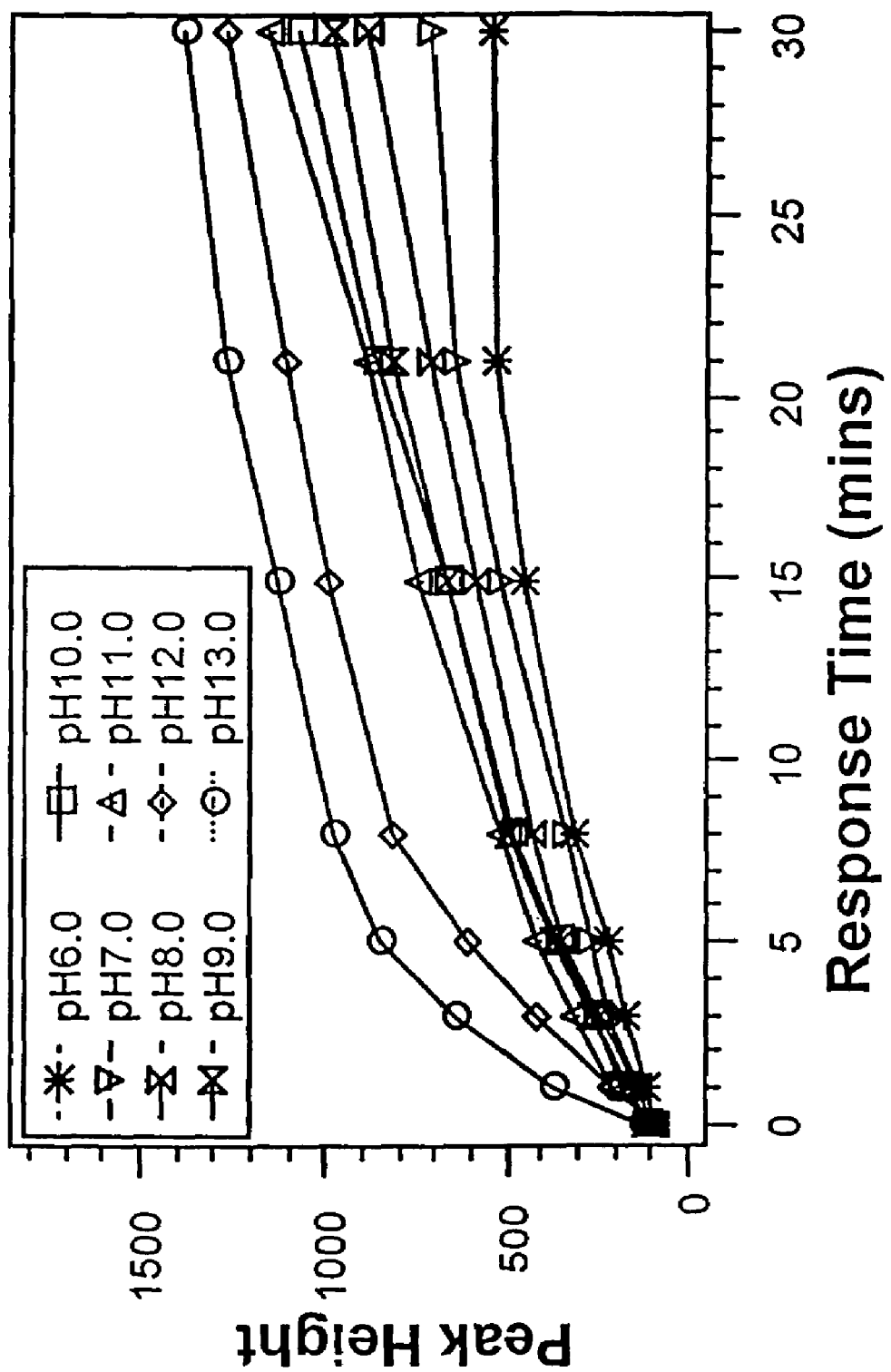
FIG. 9 shows the effect of pH on the temporal response of an optic sensor of the present invention.

The response time of the sensor is the most crucial characteristic of detectors and sensors for real-time monitoring. Yang, Y. C., et al., *Chemical Reviews*, 92:1729-1743 (1992). A study was performed using a sensor with a 200 micron coat to determine the effect of pH on the response time and on solutions of PMP prepared with pH values ranging from about 4.5 to 13 over a period of 24 hours. FIG. 9 shows the response of the sensor over the initial 30 minute time period. Additional readings were obtained for each pH value at 1 hour and at 24 hours. (Since these points remained at the same value they were excluded for reasons of clarity.) The sensors show a positive response to the presence of PMP after 3 minutes for all pH values from 6 to 12, and a positive response after 1 minute for the solution with a pH of 13. At low values of pH (below 6), the response of the sensor is indicative of the removal of PMP from the sensor. This demonstrates the washing process that occurs under acidic conditions. Neutral and slightly basic values (pH from 6-11) provide a response that is consistent over the entire pH range. The full response time for this sensor is 30 minutes. (Response times are typically reported as the time it takes the sensor to reach 80% of maximum.) Report "Assessment of Chemical and Biological Sensor Technologies," National Research Council (1984). The response at pH=12 was faster than the response at lower pH levels and had a steeper, more linear response over the initial range of concentration. At this pH, the capacity response time of the sensor was 15 minutes.

Figure 10:
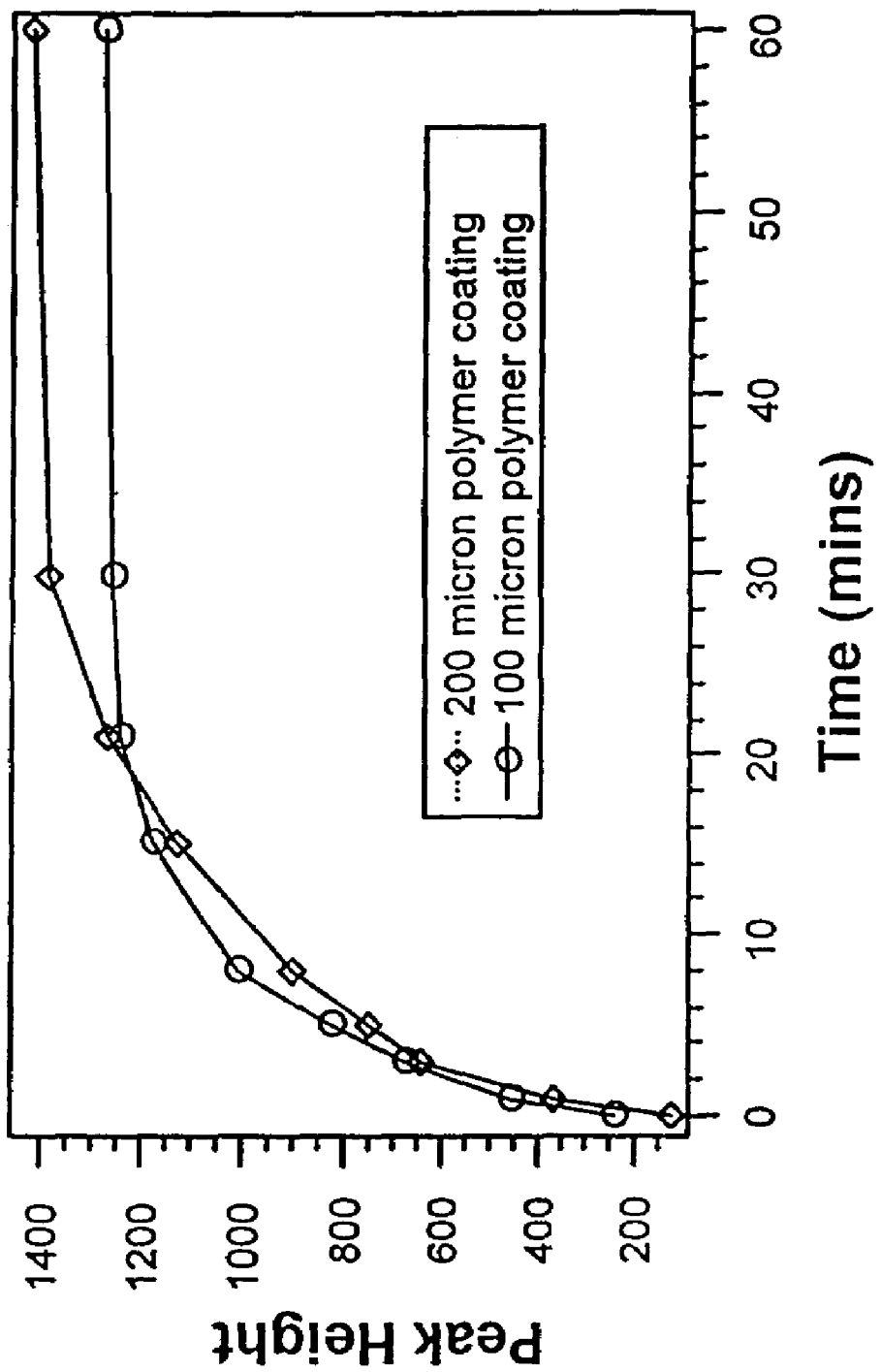
FIG. 10 shows the effect of the thickness of the polymer coating on temporal response.

The fastest response time for a sensor with a 200 micron coat was obtained using a PMP solution adjusted to pH of about 13 with NaOH. Using this pH, a capacity response time of 14 minutes was obtained. These results indicate that the more basic the solution, the faster the response time of the sensor. Since the response of the sensor will be based on the hydrolysis of the agents, the strongly alkaline solution used for the hydrolysis of the nerve agents will also enhance the response time of the sensor. (All solutions above pH 6 were prepared using deionized water, 1 M sodium hydroxide, and PMP.) The effect of coating thickness on the response time of the sensor was also evaluated. FIG. 10 shows the response of a sensor coated with a 100 micron layer and that of a sensor coated with a 200 micron layer to a 10 ppm PMP solution at pH=13. As previously stated, the fiber with a 200 micron coat reaches a maximum response within 14 minutes. The 80% response time of the 100 micron coated fiber is decreased to 8 minutes. For an on-line monitor, the time for initial response is the most important factor. Using pH=13, a distinct response occurred within 1 minute.

Example 6

Interferents

The compounds that are most chemically analogous to nerve agents are organophosphorus pesticides and herbicides. Many of these compounds exist as liquids, oils or solids at ambient temperatures. Several common pesticides, along with those most chemically similar to the agents sarin and soman were tested using the sensor in order to determine the degree of interference from each pesticide. The concentration used for screening 1000 ppm, is much higher than typically found in water systems even with runoff from nearby agriculture. The pesticide dichlorvos, commonly found in flea collars, was also screened as a possible interference.

Figure 11:
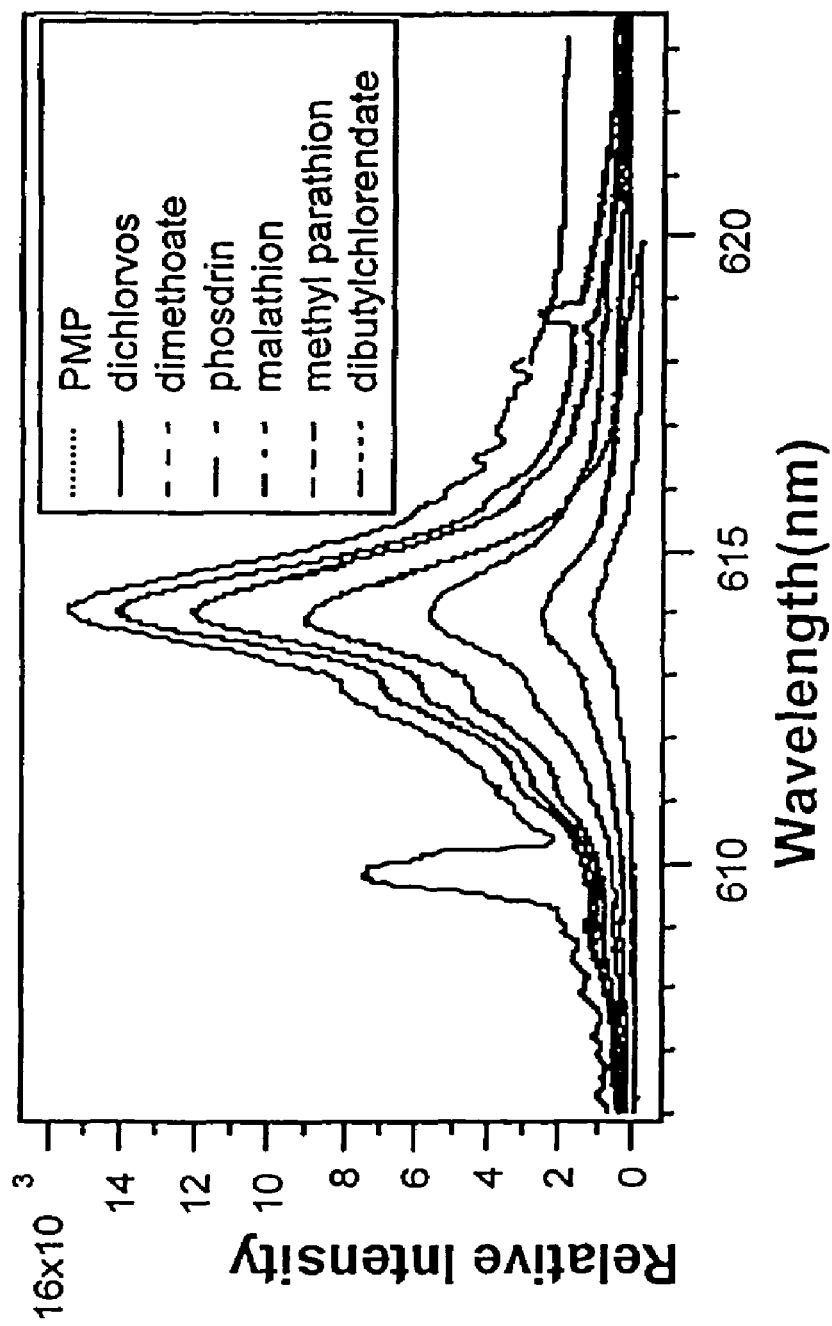
FIG. 11 shows response of an optical sensor of the present invention to selected interferents (pesticides) excited at 465.8 nm.

Each of the pesticides and a sodium phosphate solution was exposed to the sensor prepared in the above Examples for an hour with measurements taken during scheduled intervals. None of the pesticides produced a luminescence peak in the region of the PMP peak. The spectra resulting from the exposure of selected pesticides (concentration 1000 ppm) with the sensor are shown in FIG. 11. The spectrum of the sensor with 100 ppm of the hydrolysis product is shown for comparison purposes. The influence of these chemicals is apparent as indicated by the changing intensity of the major 617 nm europium luminescence band. Diclilorvos, the pesticide most structurally similar to the nerve agents, exhibited a response to the sensor with a weak band centered at 621.5 nm. This resulting band does not inhibit the acquisition or detection of the agents by the sensor. Since the chemicals that are the most likely interferences do not cause false positive readings, other less similar compounds should be unlikely to interfere. In addition, none of the pesticides screened were irreversibly bound to the sensor so poisoning is not a concern.

Example 7

Miniaturization

The device based on an Ocean Optics spectrometer exhibited favorable sensitivity and selectivity in detecting the agents on a smaller scale. Using the miniature spectrometer, the entire instrument fits on a board 3.5'×2.5'. The limit of detection for this device was determined using the same procedure used to determine the limit of detection for the larger system. This system provides a limit of detection of 7 parts per trillion using approximately 1 mW of 465.8 nm laser power and an integration time of 500 microseconds. The linear dynamic range of the device is from 7 ppt to 1 ppm using a 75 μm coating of fiber. Although the thinner coating limits the number of sites available for rebinding thereby limiting the upper end of the dynamic range, it provides a faster response time for the sensor, on the order of 1 minute at a pH of 12. Three averages were used for the determination of detection limit. Signal averaging and smoothing using the Savitzsky-Goulay method was kept to a minimal 3 point average to get the required resolution. Figures of merit for this device are presented in Table 1.

TABLE 1

Comparison of the Analytical Figures of Merit for the Two Systems

| | Lab Bench System | Portable System |
| --- | --- | --- |
| Limit of Detection | 660 ppq | 7 ppt |
| Linear Dynamic Range | 750 ppq to 10 ppm | 10 ppt to 10 ppm |
| Correlation Coefficient ($r^2$) | 0.9984 | 0.9973 |
| Slope | 1.949 counts $ppt^{-1}$ | 1.484 μV $ppt^{-1}$ |
| 80% Response Time | 8 minutes | 8 minutes |

Although specific features of the invention are shown in some drawings and not others, this is for convenience only as each feature may be combined with any or all of the other features in accordance with the invention. It will be appreciated that variations thereof can be readily perceived by those skilled in the art, which variations are nevertheless within the scope of the invention as defined by the following claims.

What is claimed is:

1. A fiber optic sensor device for detecting the presence of an organophosphorus compound, the sensor comprising:
    at least one optical fiber having a proximal end and a distal end for transmitting light energy, the proximal end being disposed within a probe housing;
    a MIP containing a lanthanide-complex disposed on the distal end of the optical fiber, wherein the lanthanide-complex is capable of chemically binding with said organophosphorus compound;
    a light source for generating excitation energy, said light source operatively associated with said optical fiber such that said excitation energy passes through said optical fiber; and
    a detector operatively associated with said optical fiber, for detecting an emission signal generated by said lanthanide complex.

2. The device of claim 1, wherein the light source is selected from the group consisting of an argon laser, blue laser, tunable laser, and light emitting diode.

3. The device of claim 1, wherein the detector means is selected from the group consisting of a spectrophotometer, spectrometer (gas or mass), photomultiplier tube, monochromator equipped with a CCD camera, filters, and the naked eye.

4. The device of claim 1, wherein the lanthanide is selected from the group consisting of: lanthanum, cerium, praseodymium, neodymium, promethium, samarium, europium, gadolinium, terbium, dysprosium, holmium, erbium, thulium, ytterbium, and lutetium.

5. The device of claim 4, wherein the lanthanide is europium or terbium.

6. The device of claim 1, wherein the distal end of the sensor is enclosed within a semi-permeable membrane.

7. The device of claim 1, wherein the organophosphorus compound is a member selected from the group consisting of soman, sarin, tabun, VX, malathion, parathion, paraoxon, diazinon and hydrolysis products thereof.

8. The device of claim 1, wherein the organophosphorus compound is pinacolylmethylphosphonate.

9. A sensor device for detecting an analyte comprising at least one optical fiber having disposed thereon a molecularly imprinted polymer containing a lanthanide-complex capable of chemically binding the analyte to be detected, said optical fiber having operatively associated therewith:
    a light source for generating excitation energy for said lanthanide-complex; and
    a detector for detecting luminescent energy generated by said lanthanide-complex upon excitation.

10. The sensor device of claim 9 wherein said lanthanide-complex comprises a lanthanide ion derived from a lanthanide selected from the group consisting of lanthanum, cerium, praseodymium, neodymium, promethium, samarium, europium, gadolinium, terbium, dysprosium, holmium, erbium, thulium, ytterbium, and lutetium.

11. The sensor device of claim 10 wherein said lanthanide ion is europium or terbium ion.

12. The sensor device of claim 11 wherein said lanthanide ion is a +3 europium ion.

13. The sensor device of claim 11 wherein the lanthanide ion is chelated with the polymerized derivate(s) of one or more ligands selected from the group consisting of 4-vinyl benzoic acid, methyl-3,5-divinyl benzoate, 4-vinyl-2-hydroxybenzaldehyde oxime, and 2-hydroxy-1,2-di-4-vinylphenylethanone (benzoin oxime vinyl derivative).

14. The sensor device of claim 13 wherein the light source is selected from the group consisting of an argon laser, blue laser, tunable laser, light emitting diode, and combinations of two or more thereof.

15. The sensor device of claim 14 wherein the light source is a light emitting diode.

16. The sensor device of claim 15 wherein the detector is selected from the group consisting of a spectrophotometer, spectrometer, photomultiplier tube, monochromator equipped with a CCD camera, filters, the naked eye, and combinations of two or more thereof.

* * * * *